United States Patent [19]
Jang et al.

[11] Patent Number: 4,894,236
[45] Date of Patent: Jan. 16, 1990

[54] DIRECT COMPRESSION TABLET BINDERS FOR ACETAMINOPHEN

[75] Inventors: Choong-Gook Jang, 2 Michelle La., Warren, N.J. 07060; Yoon Im, North Brunswick, N.J.

[73] Assignee: Choong-Gook Jang, New Brunswick, N.J.

[21] Appl. No.: 142,909

[22] Filed: Jan. 12, 1988

[51] Int. Cl.$^4$ .............................................. A61K 9/26
[52] U.S. Cl. .................................. 424/470; 424/476; 424/502
[58] Field of Search ............... 424/468, 469, 470, 476, 424/469, 468, 470, 502

[56] References Cited

U.S. PATENT DOCUMENTS

| | | | |
|---|---|---|---|
| 3,873,694 | 3/1975 | Kanig | 514/557 |
| 4,327,076 | 4/1982 | Puglia et al. | 514/251 |
| 4,327,077 | 4/1982 | Puglia et al. | 424/441 |
| 4,375,468 | 1/1983 | Dunn | 424/468 |
| 4,401,665 | 8/1983 | Sheinaus et al. | 514/617 |
| 4,439,453 | 3/1984 | Vogel | 424/465 |
| 4,562,024 | 12/1985 | Rogerson | 514/562 |
| 4,590,062 | 5/1986 | Jang | 424/469 |
| 4,661,521 | 4/1987 | Salpekar et al. | 424/465 |
| 4,670,251 | 6/1987 | Blanco | 424/465 |
| 4,704,269 | 11/1987 | Korab | 424/486 |

OTHER PUBLICATIONS

"Problem Solver" A reference manual by FMC Corp. p. IV-A-11.

*Primary Examiner*—Thurman K. Page
*Attorney, Agent, or Firm*—Roland A. Dexter

[57] ABSTRACT

Dry, directly compressed tablets are provided by a blend of from 60 to 90 weight percent of acetaminophen and from 10 to 40 weight percent of non-ionizable lipid having a melting point of from 55° C. to 80° C. The preferred lipid is hydrogenated cotton seed oil. The tablets are characterized by a hardness of at least 5 kgs. When produced by a conventional tabletting machine using a pressure of 1.5 to 20 tons per square inch.

6 Claims, No Drawings

DIRECT COMPRESSION TABLET BINDERS FOR ACETAMINOPHEN

BACKGROUND OF THE INVENTION

This invention relates to compositions and processes for making dry direct compression talets containing medicaments suitable for oral ingestion. More particular, it relates to dry, directly compressed tablets containing acetaminophen which are suitable for oral ingestion.

DESCRIPTION OF THE PRIOR ART

Acetaminophen is in common usage as a biologically active pharmaceutical which can be orally ingested in both tablet and capsule form as both an analgesic and antipyretic. It is particularly difficult to produce a directly compressed oral dosage tablet of the acetaminophen. Because the drug itself does not compress and in normal dosage levels requires very high weight percent of the drugs for a useful tablet size meaning only low amounts of excipients. Therefore, the tablet manufacturers generally purchase the acetaminophen as a pregranulated mixture with one or more suitable expients whereby the direct compression tablet formation is facilitated.

U.S. Pat. No. 3,279,998 discloses various methods for sustained release tablet formation including one containing acetaminophen (see Example 1 Col. 4) utilizing solid lipid materials such as glyceryl monostearate as the sustained release material. Although the patentees acknowledge the use of additional fillers or excipients, they show the use of a biologically active material (salicylamide in example) as the cobinder with the lipid whereby the acetaminophen can be formulated into a useful dry direct compression sustained release tablet. Unfortunately, the combination of acetaminophen and glyceryl monostearate in the component ratio of Example 1 (when the salicylamide is left out) does not produce a useful, dry, directly compressed tablet when using a standard tablet press. A useful, dry, directly compressed tablet containing predominantly acetaminophen can be obtained according to U.S. Pat. No. 4,590,062 (see Table VI, col. 6) when the excipient binders are a neutral lipid and ethyl cellulose. Unfortunately, increasing the weight percent of acetaminophen in the tablet to the range of about 90 percent results in a tablet of such reduced hardness, i.e. less than 5 kg. that it is not useful.

It is therefore an object of this invention to provide a dry, directly compressed tablet containing high dosage levels of acetaminophen and having a hardness of at least five (5) kilograms on Pfizer Hardness Tester.

SUMMARY OF THE INVENTION

It has been discovered that a dry mixture of 83.5% by weight of acetaminophen and 16.5% by weight of hydrogenated cottonseed oil sold by Capital City Products as Dritex® can be directly compressed into a tablet having a hardness of at least 5 kg. when compressed in a conventional drug tabletting machine by a conventional pressure of 7000 pounds per square inch.

In accordance with this invention there is provided a dry directly compressed product comprising from 60 to 90, preferably from 70 to 85 weight percent of acetaminophen and from 10 to 40, preferably from 15 to 30 weight percent of a powdered and non-ionizable lipid having a melting point of 55° C. to 80° C., preferably from 60° C. to 70° C. To produce this product of the invention, one uses a process comprising the steps of dry blending from 60 to 90, preferably 70 to 85 weight percent of granular acetaminophen and from 10 to 40, preferably 15 to 30, weight percent non-ionizable lipid in powder form, compressing said blend under a pressure of 1.5 to 20 tons per square inch, and thereafter recovering said blend as a compressed product having a hardness of at least 5 kilograms.

DETAILED DESCRIPTION OF THE INVENTION

From the foregoing, it must be evident that a dry, directly compressed tablet containing predominantly acetaminophen can be readily realized by the practice of this invention utilizing a limited class of non-ionizable lipids of narrow melting points as a binder matrix for the acetaminophen. The acetoaminophen crystals are substantially non-compressible when subjected to conventional tabletting machines. This property of non-compressibillity has caused the acetaminophen to be marketed both as a pure grade for wet granulation and also in pregranulated combination with one or more excipients to facilitate its direct compression tabletting alone or with other biologically active agents.

Further, the acetaminophen can be used in the practice of this invention in combination with up to ten(10) weight percent of othe biological agents as long as it does not significantly contribute to the tablet hardness. Salicylamide in U.S. Pat. No. 3,279,998 does help binding which is shown by the hardness increase (see Table II and III). The acetaminophen useful for our teachings is crystalline particulate, has a purity of 98% or higher and a size of no greater than 20 mesh.

NON-IONIZABLE LIPIDS

In accordance with this invention, the useful non-ionizable lipid has a melting point of from 55° C. to 80° C., preferably 60° C. to 70° C., with an non-ionizable structure which is suitable for dry blending and upon compression can deform and diffuse into the void spaces between acetaminophen crystals and glue them together as a result of van der Waal's forces. A possible explanation of the invention is that the acetaminophen and lipid cooperate upon dry compression much like a stone/cement mixture where a proper weight ratio range between the weight percents of stone and cement is required for the best strength whereas each component separately has a weak structure. Table III shows that each component of this invention has a poor hardness of less than 5 kg.

Yet when they are dry blended and compressed, the combination shows usuable hardnesses i.e. greater than 5 kgs. (see Table I and II.) The lipid as well as the dry blend should have a particle size of no greater than 20 mesh, preferably 30 mesh. The dry blend combination of acetaminophen and lipid contains from 10 to 40 preferably from 15 to 30, weight percent of the lipid whereby a matrix of the lipid about the acetaminophen is realized upon direct compression of 1.5 to 20 tons per square inch that a tablet of the compressed blend having a hardness of at least 5 kgs. is realized.

The useful lipid with a melting point of 55° C. to 80° C., preferably 60° C. to 70° C., should be non-ionizable and deformable and diffusible upon pressure; yet after pressure is applied remain solid to maintain the structure. The lipid is exemplified by neutral lipids (mono-, di, tri-glycerides of fatty acids) and other esters of fatty acids such as hydrogenated cotton seed oil which has been obtained from Capital City Product as Dritex and Sterotex and from Witco Chemical as Neustrene and Durkee as Lubritab; aliphatic alcohols of carbon numbers 14 to 24 such as stearyl alcohol; fatty amides such as oleylpalmitamide; hydrocarbon waxes of carbon numbers 25 to 40 such as n-Triacontane; and derivatives of those mentioned above and other fatty material.

The following examples demonstrate the practice of the invention and utility of this invention.

EXAMPLE 1

TABLE I

Acetaminophen Tablet Formation Measured by Hardness & the Degree of Capping with Various Excipients.

| Excipients | m.p. (°C.) | Hardness (kg) | Degree of Capping (%)** |
|---|---|---|---|
| Dritex ® | 60–63 | 6.1 | 0 |
| Stearic Acid | 66.5–68.0 | 6.3 | 50 |
| Carnauba Wax | 81–86 | 4.6 | 35 |
| Micro crystalline Cellulose* | | | 100 |
| Dicalcium Phosphate* | | | 100 |
| Lactose* | | | 100 |
| Ethylcellulose+ | | | 100 |
| Starch* | | | 100 |
| Binding Mixtures of Example 1. of U.S. Pat. No. 4,059,062 | | 4.8 | 25% |

All tablets were made by dry blending and dry compression with excipients and acetaminophen U.S.P (99%) on a rotary tablet press under 3.5 ton; tablet wt. 1.03 grm.; Compositions: 83.5% acetaminophen/16.5% excipient by weight.
*Commercially widely used direct compression grade excipients used for direct compresion production of tablets involving other medicaments; Hardness in kg. on a Pfizer hardness tester (average of 5 tablets)
**the degree of capping (%)(average of 10 tablets.), see PROBLEM SOLVER and reference manual by FMC Corp. page IV-A-11.
+Patent application pending for other biologically active agents.

Table I shows that only Dritex ® is useful for dry direct compression tablets of acetaminophen whereas other commonly used excipients fail.

EXAMPLE 2

In this example. six different formulations were tabletted to determine useful ones which to be useful should have a hardness of at least 5 kg.

TABLE II

Contribution to Hardness by Self-Compressible drug Salicylamide for Acetaminophen Tablets (see * for U.S. Pat. No. 3,279,998 by Raff et al).

| | Compositions (wt. in gram) | | | | | |
|---|---|---|---|---|---|---|
| Acetaminophen | 238.5 | 97.5* | — | 238.5 | 97.5 | — |
| Salycylamide | — | 141 | 238.5 | — | 141 | 238.5 |
| Glyceryl Mono-Stearate | 33 | 33 | 33 | | | |
| Dritex | | | | 33 | 33 | 33 |
| Total | 271.5 | 271.5 | 271.5 | 271.5 | 271.5 | 271.5 |
| Hardness (kg) | 4.4 | 6.8 | 9.1 | 5.9 | 8.4 | 9.8 |

Tabletting conditions and processes same as those disclosed in Table I.

Table II shows that the increase of salicylamide increases hardness of tablets to useful hardnesses. However, with or without salicylamide, Dritex can provide the tablet of useful hardnesses.

EXAMPLE 3

Six additional formulations were tabletted.

TABLE III

Salicylamide as a Tablet Binder for Acetaminophen measured by Hardness.

| | Compositions (wt. %) | | | | | |
|---|---|---|---|---|---|---|
| Acetaminophen | 100 | 70.4 | 20.4 | 0 | 61.9% | |
| Salicylamide | 0 | 29.6 | 79.6 | 100 | 26 | |
| Glycecylmono-Stearate | — | — | — | — | 12.1 | |
| Dritex | — | — | — | — | — | 100 |
| Total | 100 | 100 | 100 | 100 | 100 | 100 |
| Hardness (kg.) | 3.8 | 4.1 | 6.7 | 8.3 | 5.5 | 4.8 |

Tabletting process & conditions same as those disclosed in Table I.

Table III shows that salicylamide of itself can form direct compression, useful tablets with acetaminophen which the formulation is predominantly salicylamide. The table further shows the Dritex itself does not compress to a useful hardness.

EXAMPLE 4

In some instances, this invention can be used advantageously to overcome the disadvantages inherent in the teachings of U.S. Pat. No. 4,601,894.

It has been discovered that highly water-soluble, biologically active materials can be used in combination with biologically active materials of low water solubility by combining the teachings herein with those of U.S. Pat. No. 4,590,062 to provide a multilayered heterogenous tablet which yields to the blood stream appropriate and predictable levels of both the high and low water soluble active materials. This is seen from the following example (Table IV and V) which table is produced by the condition and process as disclosed in Table I except that each formulation is separately layered one onto the other into the die cavity prior to imposing the tabletting pressure. In Table V, T100% is calculated from Cumulative % Released $= k \text{ (time)}^{\frac{1}{2}}$ where k is a proportionality constant.

TABLE IV

Two Layered Tablet for Acetaminophen/Dexbrompheniramine Maleate/Pseudoephedrine HCl utilizing this invention and U.S. Pat. No. 4,590,062.

| | Composition (wt. %) |
|---|---|
| 1st Layer: | |
| Acetaminophen | 84.0 |
| Dexbrompheniramine Maleate | 0.9 |
| Dritex | 14.0 |
| Magnesium Stearate as Lubricant | 1.1 |
| Total | 100.0 |
| 2nd Layer: | |
| Pseudoephedrine HCl | 12.1 |
| Acetaminophen | 40.3 |
| Dritex | 40.3 |
| Ethylcellulose | 5.1 |
| Aerosil R-971 | 1.2 |
| Magnesium Stearate as Lubricant | 1.0 |
| Total | 100.0 |

The resulting tablets had the drug release rates shown in Table V.

TABLE V

Drug Release Rates for the Tablet of Table IV.

| Drugs | Cumulative Amounts (%) Drug Released in 4 Hours | Projected T 100% (Hours) |
|---|---|---|
| Acetaminophen | 70.3 | 8.1 |
| Pseudoephedrine HCl | 71.7 | 7.8 |

TABLE V-continued

Drug Release Rates for the Tablet of Table IV.

| Drugs | Cumulative Amounts (%) Drug Released in 4 Hours | Projected T 100% (Hours) |
| --- | --- | --- |
| Dexbrompheniramine Maleate | 50.5 | 15.7 |

To summarize this invention, the non-ionizable lipids of narrow melting points provide the function of direct compression tablet binder (as well as sustained release material if desired) for high potency acetaminophen tablets. As shown in Table II and III, Example 1 in U.S. Pat. No. 3,279,998 uses salicylamide as a cobinder although it is not mentioned because pure salicylamide has the greatest hardness and the hardnesses of the acetaminophen combination falls between the hardnesses of two components. In this invention, the hardness of the resultant tablet is greater than those of individual components which is unexpected from prior arts.

In the course of making this directly compressed tablet, one can add usual tabletting additives such as disintegrants, flow aiding materials and lubricants up to 10 weight percents of the tablet weight (see PROBLEM SOLVER and reference manual on tablet compression by FMC Corp. and the article by Gordon, M. and Chowhan, T. J. of Pharmaceutical Sciences Vol. 76, p. 907, 1987 for additives).

What is claimed is:

1. A dry, direct, compressed product consisting essentially of from 60 to 90 weight percent of acetoaminophen and from 10 to 40 weight percent of hydrogenated cottonseed oil whereby said product has a hardness of at least 5 kilograms.

2. The product according to claim 1 wherein said acetoaminophen is present in from 70 to 85 weight percent and said oil is present in from 15 to 30 weight percent.

3. The product according to claim 1 wherein said acetoaminophen is present in about 83.5 weight percent and said oil is present in about 16.5 weight percent.

4. The product according to claim 1 which also contains up to 10% of an additional biologically active material selected from the group consisting of salicylamide, dexbrompheniramine maleate, psuedoephedrine HCl and mixtures thereof, said weight percent based on the weight of the acetoaminophen.

5. A method for producing a tablet containing acetoaminophen comprising the steps of: dry blending
   (a) from 60 to 90 weight percent crystalline acetoaminophen containing from 0 to less than 10 percent by weight of a biologically active material selected from the group consisting of salicylamide, dexbrompheniramine maleate, pseudoephrine HCl and mixtures thereof, and
   (b) from 10 to 40 weight percent of lipid in powder form having a particle size no greater than 20 mesh, said lipid having a melting point ranging from 55° to 80° C. and selected from the group consisting of neutral esters of fatty acids, aliphatic alcohols of carbon numbers 14 to 24, fatty amides, hydrocarbon waxes of carbon numbers 25 to 40 and derivatives thereof; compressing said blend under a pressure of 1.5 to 20 tons per square inch; recovering said blend as a compressed product having a hardness of at least 5 kilograms on a Pfizer hardness tester.

6. The method according to claim 5 wherein said lipid is hydrogenated cottonseed oil.

* * * * *